US010543281B2

(12) United States Patent
Aoki et al.

(10) Patent No.: US 10,543,281 B2
(45) Date of Patent: *Jan. 28, 2020

(54) PHARMACEUTICAL COMPOSITION CONTAINING CAMPTOTHECIN POLYMER DERIVATIVE

(71) Applicant: Nippon Kayaku Kabushiki Kaisha, Tokyo (JP)

(72) Inventors: Shin Aoki, Tokyo (JP); Shinya Fujita, Tokyo (JP)

(73) Assignee: Nippon Kayaku Kabushiki Kaisha, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/752,923

(22) PCT Filed: Aug. 25, 2016

(86) PCT No.: PCT/JP2016/074762
§ 371 (c)(1),
(2) Date: Feb. 15, 2018

(87) PCT Pub. No.: WO2017/038607
PCT Pub. Date: Mar. 9, 2017

(65) Prior Publication Data
US 2018/0236091 A1 Aug. 23, 2018

(30) Foreign Application Priority Data
Sep. 3, 2015 (JP) ................................ 2015-173755

(51) Int. Cl.
A61K 47/60 (2017.01)
A61K 47/26 (2006.01)
A61K 31/4745 (2006.01)
A61K 47/54 (2017.01)
A61K 9/19 (2006.01)
A61K 47/64 (2017.01)
A61P 35/00 (2006.01)

(52) U.S. Cl.
CPC ............... A61K 47/60 (2017.08); A61K 9/19 (2013.01); A61K 31/4745 (2013.01); A61K 47/26 (2013.01); A61K 47/542 (2017.08); A61K 47/645 (2017.08); A61P 35/00 (2018.01)

(58) Field of Classification Search
None
See application file for complete search history.

(56) References Cited

U.S. PATENT DOCUMENTS

| 8,334,364 | B2 | 12/2012 | Yamamoto et al. | |
| 9,855,339 | B2* | 1/2018 | Fujita | A61K 47/42 |
| 9,993,569 | B2* | 6/2018 | Fujita | A61K 47/42 |
| 2003/0148931 | A1 | 8/2003 | Takahashi et al. | |
| 2005/0215485 | A1 | 9/2005 | Ito et al. | |
| 2006/0067910 | A1 | 3/2006 | Kitagawa et al. | |
| 2009/0239782 | A1 | 9/2009 | Nakamura et al. | |
| 2010/0004403 | A1 | 1/2010 | Kitagawa et al. | |
| 2011/0110881 | A1 | 5/2011 | Kataoka et al. | |
| 2012/0231053 | A1 | 9/2012 | Akatsu et al. | |
| 2017/0298190 | A1 | 10/2017 | Fujita et al. | |
| 2018/0078653 | A1 | 3/2018 | Fujita et al. | |

FOREIGN PATENT DOCUMENTS

| EP | 2204398 A1 | 7/2010 |
| EP | 2305275 A1 | 4/2011 |
| EP | 3238730 A1 | 11/2017 |
| JP | 2005-523329 A | 8/2005 |
| RU | 2315782 C2 | 1/2008 |
| WO | 2002/005855 A1 | 1/2002 |
| WO | 20041039869 A1 | 5/2004 |
| WO | 2008/010463 A1 | 1/2008 |
| WO | 20081041610 A1 | 4/2008 |
| WO | 2008/056596 A1 | 5/2008 |
| WO | 2009/142328 A1 | 11/2009 |
| WO | 2011/049042 A1 | 4/2011 |
| WO | 2015/125641 A1 | 8/2015 |

OTHER PUBLICATIONS

International Search Report and Written Opinion dated Sep. 27, 2016 in corresponding PCT application No. PCT/JP2016/074762.
International Preliminary Report on Patentability dated Mar. 6, 2018 in corresponding PCT application No. PCT/JP2016/074762.
European communication dated Apr. 8, 2019 in corresponding European patent application No. 16841639.4.
Bala et al., "Prodrug and Nanomedicine Approaches for the Delivery of the Camptothecin Analogue SN38", Journal of Controlled Release, vol. 172, pp. 48-61, 2013.
Gong et al., "Polymeric Micelles Drug Delivery System in Oncology", Journal of Controlled Release, vol. 159, pp. 312-323, 2012.
Koizumiet at al., "Novel SN-38-Incorporating Polymeric Micelles, NK012, Eradicate Vascular Endothelial Growth Factor-Secreting Bulky Tumors", Cancer Research, vol. 66, pp. 10048-10056, Oct. 15, 2006.

(Continued)

Primary Examiner — Zinna Northington Davis
(74) Attorney, Agent, or Firm — Nields, Lemack & Frame, LLC

(57) ABSTRACT

Provided is a pharmaceutical preparation including a polymerized camptothecin derivative that is obtained by bonding a camptothecin derivative having nanoparticle-forming properties by associating in an aqueous solution, to a polymer carrier, the pharmaceutical preparation composition having enhanced preparation stability. Particularly, a pharmaceutical preparation maintaining nanoparticle-forming properties and camptothecin derivative bonding stability, which are important factors, and having excellent storage stability is provided. Disclosed is a pharmaceutical preparation including a block copolymer in which a polyethylene glycol segment is linked to a polyglutamic acid segment including a glutamic acid unit having a camptothecin derivative bonded thereto; and a saccharide. The pharmaceutical preparation forms associates in an aqueous solution, and the ratio of change in the scattered light intensity of the associates of the pharmaceutical preparation obtained after the pharmaceutical preparation is stored for 4 weeks at 40° C. under light-shielded conditions, is 20% or less.

8 Claims, No Drawings

(56) References Cited

OTHER PUBLICATIONS

Matsumura, "Poly (Amino Acid) Micelle Nanocarriers in Preclinical and Clinical Studies", Advanced Drug Delivery Reviews, vol. 60, pp. 899-914, 2008.
Matsumura, "Preclinical and Clinical Studies of NK012, an SN-38-Incorporating Polymeric Micelles, Which is Designed Based on EPR Effect", Advanced Drug Delivery Reviews, vol. 63, pp. 184-192, 2011.
Matsumura, "Polymeric Micellar Delivery Systems in Oncology", Japanese Journal of Clinical Oncology, vol. 38, pp. 793-802, 2008.
Russian communication, with English translation, dated Aug. 16, 2019 in corresponding Russian patent application No. 2018102756/04.

* cited by examiner

PHARMACEUTICAL COMPOSITION CONTAINING CAMPTOTHECIN POLYMER DERIVATIVE

TECHNICAL FIELD

The present invention relates to a pharmaceutical preparation composition of a polymerized camptothecin derivative produced by bonding a camptothecin derivative to a polymer carrier, the pharmaceutical preparation composition having enhanced preparation stability. The polymerized camptothecin derivative has a property by which multiple molecules of the derivative become associative in an aqueous solution and thereby form nanoparticles. The present invention is a technology relating to a pharmaceutical preparation containing a polymerized camptothecin derivative having such nanoparticle-forming properties, the pharmaceutical preparation having excellent storage stability of maintaining the nanoparticle-forming properties for a long time.

BACKGROUND ART

In order to effectively exhibit the efficacy of a pharmaceutical product, it is required to cause a pharmacologically active compound to effect at an appropriate site in the body at an appropriate concentration for an appropriate length of time. Particularly, a cytotoxic antitumor agent is such that when systematically administered by intravenous administration or the like, the cytotoxic antitumor agent is widely distributed over the whole body and exhibits cell proliferation inhibitory action. In this case, it is reported that since cells are subjected to the pharmacologically active action without distinction between cancer cells and normal cells, serious side effects are brought about by the effect on normal cells. Therefore, in order to reduce side effects, a technology of transporting the antitumor agent to a tumor lesion is important. Thus, there is a demand for a method for controlling the pharmacokinetics in order to selectively transport an antitumor agent to a tumor tissue and to cause the antitumor agent to act at an appropriate drug concentration for an appropriate drug sensitization time.

As a method for controlling the pharmacokinetics, a method of utilizing the pharmacokinetic characteristics based on the molecular weight is known. That is, when a biocompatible polymer material is intravascularly administered, renal excretion is suppressed, and a long half-life in blood is maintained. Furthermore, since tumor tissues have high tissue permeability of polymer materials, and since recovery mechanism of polymer materials is not sufficiently constructed, it is known that polymer materials are distributed and concentrated in tumor tissues at relatively high concentrations. Thus, development of polymerized antitumor agents in which a biocompatible polymer material is used as a polymer carrier and an antitumor agent is bonded to this polymer carrier, has been implemented.

As the polymerized antitumor agents, polymerized antitumor agents have been reported, in which a block copolymer obtained by linking a polyethylene glycol segment and a polyglutamic acid segment is used as a polymer carrier, and various antitumor agents are bonded to side-chain carboxylic acids of the polyglutamic acid segment. Patent Literature 1 discloses a pharmaceutical product in which 7-ethyl-10-hydroxycamptothecin is bonded to the relevant block copolymer. Furthermore, as other antitumor agents, a block copolymer conjugate of a cytidine-based antitumor agent (Patent Literature 2), a block copolymer conjugate of combretastatin A-4 (Patent Literature 3), a block copolymer conjugate of a HSP90 inhibitor (Patent Literature 4), and the like are known. It is described that these polymerized antitumor agents have enhanced antitumor effects, compared to those low molecular weight antitumor compounds used as active ingredients.

These block copolymer conjugates of antitumor agents are polymerized antitumor agents in which hydroxyl groups of the antitumor agent are bonded to side chain carboxylic acids of the block copolymer through ester bonds to form conjugates. These are prodrugs that exhibit antitumor activity when administered into the body, by cleaving the ester bonds at a constant rate to release the antitumor agent.

Furthermore, these block copolymers having antitumor agents bonded thereto have a physical property by which, when the block region to which the antitumor agent is bonded is hydrophobic, the antitumor agent-bonded region in an aqueous solution exhibits associative properties based on a hydrophobic interaction, and multiple molecules of the block copolymer form associative aggregates.

Associative aggregates formed by this polymerized antitumor agent may be detected by a light scattering analysis using laser light or the like, and the physical properties of the associative aggregates may be measured by means of the value of scattered light intensity. That is, the physical properties of the associative aggregates may be defined by taking the scattered light intensity as a measured value.

A polymerized antitumor agent having such associative properties behaves as nanoparticles that are produced in the body based on associative properties, and thereby exhibits pharmacokinetics such as described above. Thus, the polymerized antitumor agent is distributed at a high concentration in a tumor tissue, and releases an antitumor agent, thereby exhibiting a high antitumor effect. Therefore, for these polymerized antitumor agents, the associative properties of forming nanoparticles constitute an important factor for performance demonstration.

A drug-polymer conjugate pharmaceutical product such as described above is a pharmaceutical product that promotes high pharmacological activity and reduction of side effects by means of the pharmacokinetics based on the molecular weight of the polymer carrier and by slowly releasing the drug bonded thereto in an activated form. Therefore, such a drug-polymer conjugate pharmaceutical product needs to be produced into a preparation which undergoes less change in the molecular weight of the polymer carrier in a state of being stored as a preparation, that is, a preparation having excellent storage stability with suppressed molecular weight reduction.

As a preparation provided with storage stability for a drug-polymer conjugate pharmaceutical product taken into consideration, for example, Patent Literatures 5 and 6 disclose that change in the molecular weight of the polymer carrier and liberation of the camptothecin derivative are suppressed by producing a conjugate of a polysaccharide having carboxyl groups and a camptothecin derivative into a pharmaceutical preparation including a sugar or a sugar alcohol and a pH adjusting agent.

However, in the drug-polymer conjugate pharmaceutical products described in Patent Literatures 5 and 6, it is speculated that the drug-polymer conjugate pharmaceutical products do not form strong associates in the form of nanoparticles. Thus, the molecular weight of the polymer carrier is considered to function as a performance demonstrating factor. For this reason, molecular weight reduction by a chemical decomposition reaction caused by cleavage of chemical bonds of the carrier is a problem to be solved, and this suppression is the purpose of the invention. However, in regard to a polymerized antitumor agent based on a block copolymer, which employs polymerization by producing nanoparticles from associative aggregates as a performance managing factor, a stable pharmaceutical preparation for which it is intended to control the nanoparticle-forming ability is not known.

CITATION LIST

Patent Literature

Patent Literature 1: WO 2004/039869 A
Patent Literature 2: WO 2008/056596 A
Patent Literature 3: WO 2008/010463 A
Patent Literature 4: WO 2008/041610 A
Patent Literature 5: WO 2002/005855 A
Patent Literature 6: JP 2005-523329 W

SUMMARY OF INVENTION

Technical Problem

It is an object of the present invention to provide a pharmaceutical preparation composition of a polymerized camptothecin derivative obtained by bonding a camptothecin derivative to a polymer carrier, the pharmaceutical preparation composition having the nanoparticle-forming properties maintained for a long time and having enhanced preparation-related stability. Particularly, it is an important factor in view of performance that the polymerized camptothecin derivative has associative properties, and multiple molecules of the polymerized camptothecin derivative form associative aggregates in an aqueous solution and thus form nanoparticles. It is an object of the invention to provide a pharmaceutical preparation containing a polymerized camptothecin derivative capable of forming nanoparticles, the pharmaceutical preparation having excellent storage stability based on the associate nanoparticle-forming properties as an indicator.

Solution to Problem

The inventors of the present invention found that in regard to a polymerized camptothecin derivative based on a block copolymer in which a polyethylene glycol segment is linked to a polyglutamic acid segment including a glutamic acid unit having a camptothecin derivative bonded thereto, when a saccharide is used as an additive, the nanoparticle forming properties based on the formation of associative aggregates are controlled, and thus a pharmaceutical preparation having excellent storage stability is obtained. Thus, the inventors completed the invention. That is, the gist of the present specification includes the following inventions.

[1] A pharmaceutical preparation including a block copolymer of a polyethylene glycol segment and a polyglutamic acid segment linked together, the polyglutamic acid segment including a glutamic acid unit having a camptothecin derivative bonded thereto; and a saccharide, in which the block copolymer is a block copolymer represented by General Formula (1):

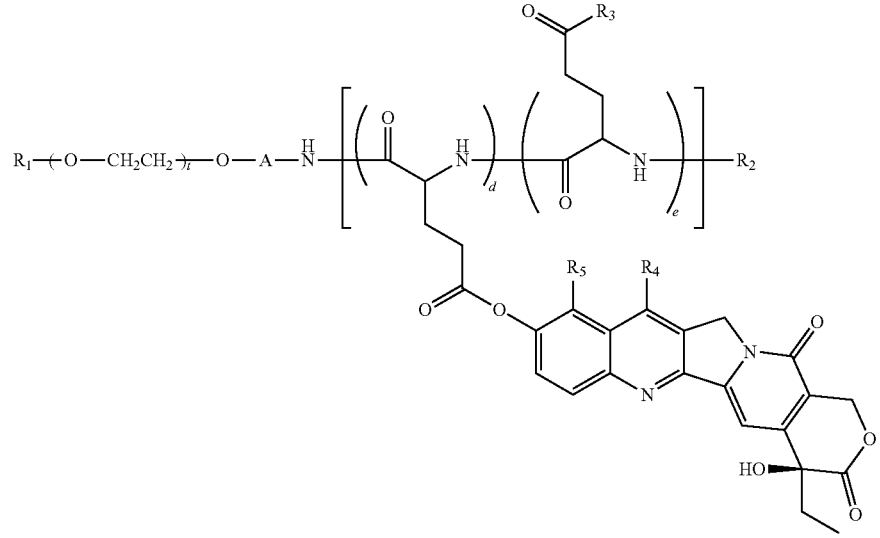

wherein $R_1$ represents a hydrogen atom or a (C1-C6) alkyl group optionally substituted with a substituent; A represents a (C1-C6) alkylene group; $R_2$ represents any one selected from the group consisting of a hydrogen atom, a (C1-C6) acyl group optionally substituted with a substituent, and a (C1-C6) alkoxycarbonyl group optionally substituted with a substituent; $R_3$ represents a hydroxyl group and/or $-N(R_4)CONH(R_7)$; $R_6$ and $R_7$ may be identical with or different from each other, each representing a (C1-C8) alkyl group optionally substituted with a tertiary amino group; $R_4$ represents any one selected from the group consisting of a hydrogen atom, a (C1-C6) alkyl group optionally substituted with a substituent, and a silyl group optionally substituted with a substituent; $R_5$ represents a hydrogen atom or a (C1-C6) alkyl group optionally substituted with a substituent; t represents an integer from 45 to 450; d and e each represent an integer, (d+e) represents an integer from 6 to 60, the proportion of d with respect to (d+e) is 1% to 100%, the proportion of e is 0% to 99%; and the polyglutamic acid segment has a polyglutamic acid segment structure having a glutamic acid unit with a camptothecin derivative bonded thereto and a glutamic acid unit with a $R_3$ group bonded thereto, with the glutamic acid units being each independently arranged randomly, wherein the pharmaceutical preparation has a physical property of forming associates based on a plurality of the block copolymer molecules in an aqueous solution, and wherein the ratio of change in the scattered light intensity of the associates of the pharmaceutical preparation obtained after the pharmaceutical preparation has been stored for 4 weeks at 40° C. under light-shielded conditions, is 20% or less.

The block copolymer according to the present invention in which a polyethylene glycol segment is linked to a polyglutamic acid segment including a glutamic acid unit having a camptothecin derivative bonded thereto is such that the polyglutamic acid segment having a camptothecin derivative bonded thereto, which is relatively hydrophobic, exhibits associative properties in an aqueous solution based on hydrophobic interaction and forms nanoparticles, which are associative aggregates formed by a plurality of the block copolymer. This is a pharmaceutical product that is administered into the body, aiming at causing the block copolymer to behave as the aforementioned associative aggregates in vivo, and to release the camptothecin derivative bonded thereto from this block copolymer at a constant rate to thereby exhibit pharmacological activity. For this reason, the block copolymer, which is a polymerized camptothecin derivative, is an important factor for exhibiting the performance of the physical property of becoming nanoparticles as a result of the formation of associative aggregates. Regarding the associative aggregates, the associate-forming property may be evaluated by measuring the scattered light intensity using laser light. Usually, this block copolymer gives a measured value of several thousand cps to several hundred thousand cps as the scattered light intensity value, and thus the block copolymer is acknowledged to form associative aggregates. The present invention is intended to use the scattered light intensity obtained by means of laser light as an index of the associative aggregate-forming properties, and to provide a pharmaceutical preparation having less change in the performance of associate formation. Therefore, the present invention may produce a pharmaceutical preparation including the polymerized camptothecin derivative, the pharmaceutical preparation having controlled nanoparticle-forming properties, which is an important factor in view of performance, and having high stability of being stably maintained during preparation storage.

[2] The pharmaceutical preparation according to [1], in which when the pharmaceutical preparation is made into an aqueous solution containing the camptothecin derivative at a concentration of 1 mg/mL, the pH of the aqueous solution is 3.0 to 6.0.

[3] The pharmaceutical preparation according to [1] or [2], further including a pH adjusting agent.

The present invention is a pharmaceutical preparation including the block copolymer and a saccharide; however, there is a possibility that when the preparation is made into an aqueous solution, the pH may vary depending on the acidity of the block copolymer, the type of the saccharide, and the respective contents of the block copolymer and the saccharide. In regard to the pharmaceutical preparation including the polymerized camptothecin derivative, in order to obtain a pharmaceutical preparation having controlled nanoparticle-forming properties, which is an important factor in view of performance, and having high stability of being stably maintained during preparation storage, it is preferable that the pH of the aqueous solution of the pharmaceutical preparation is in the range of 3.0 to 6.0. In order to adjust the aqueous solution to a suitable pH range, the type and dose of the block copolymer and/or the saccharide may be adjusted as appropriate, and depending on cases, a pH adjusting agent may also be used.

[4] The pharmaceutical preparation according to any one of [1] to [3], in which the saccharide is one or more kinds of saccharides and sugar alcohols selected from the group consisting of maltose, glucose, lactose, fructose, trehalose, sucrose, mannitol, sorbitol, inositol, xylitol, and magnesium gluconate.

[5] The pharmaceutical preparation according to any one of [1] to [4], in which the saccharide is one or more kinds of saccharides and sugar alcohols selected from the group consisting of maltose, glucose, lactose, fructose, trehalose, and sucrose.

[6] The pharmaceutical preparation according to any one of [1] to [5], in which the pharmaceutical preparation includes 10 to 500 parts by mass of the saccharide with respect to 1 part by mass of the camptothecin derivative content of the block copolymer.

[7] The pharmaceutical preparation according to any one of [1] to [6], in which the pharmaceutical preparation is a freeze-dried preparation.

Advantageous Effects of Invention

In regard to the block copolymer according to the present invention, in which a polyethylene glycol segment is linked to a polyglutamic acid segment including a glutamic acid unit having a camptothecin derivative bonded thereto, the formation of nanoparticles based on associative aggregates is an important performance for exhibiting efficacy, and it is important that the ability of forming desired associates may be maintained during the period of preparation storage. The present pharmaceutical preparation may provide a pharmaceutical preparation including the block copolymer capable of forming associates as an active ingredient, the pharmaceutical preparation having excellent storage stability in connection with the association performance. That is, a pharmaceutical preparation having guaranteed effectiveness as a pharmaceutical product, in which the block copolymer maintains desired association performance and may be used as a desired camptothecin derivative-bonded associative nanoparticle-forming body, may be provided.

DESCRIPTION OF EMBODIMENTS

According to the present invention, on the occasion of producing a pharmaceutical preparation in which the long-term stability as a pharmaceutical product of a block copolymer in which a polyethylene glycol segment is linked to a polyglutamic acid segment including a glutamic acid unit having a camptothecin derivative bonded thereto, a pharmaceutical preparation including the block copolymer, in which when a saccharide is used as an additive for the block copolymer, the ratio of change in the formation of associates of the pharmaceutical preparation obtained after storing of the pharmaceutical preparation for 4 weeks at 40° C. under light-shielded conditions is low, and the formation of associates is maintained stably, may be produced. In the following description, the present invention will be explained in detail.

The present invention uses a block copolymer in which a polyethylene glycol segment is linked to a polyglutamic acid segment including a glutamic acid unit having a camptothecin derivative bonded thereto, the block copolymer being represented by the following general formula (1):

The block copolymer is a block copolymer in which a polyethylene glycol segment is linked by an appropriate linking group to a polyglutamic acid segment including a glutamic acid unit having a camptothecin derivative bonded to a side chain by an ester bond.

The (C1-C6) alkyl group which may have a substituent with regard to $R_1$ may be a linear, branched or cyclic (C1-C6) alkyl group which may have a substituent. Examples thereof may include a methyl group, an ethyl group, a n-propyl group, an isopropyl group, a n-butyl group, a s-butyl group, a t-butyl group, a n-propyl group, a neo-pentyl group, a cyclopentyl group, a n-hexyl group, and a cyclohexyl group.

Examples of the substituent to be carried may include a mercapto group, a hydroxyl group, a halogen atom, a nitro group, a cyano group, a carbocyclic or heterocyclic aryl group, an alkylthio group, an arylthio group, an alkylsulfinyl group, an arylsulfinyl group, an alkylsulfonyl group, an

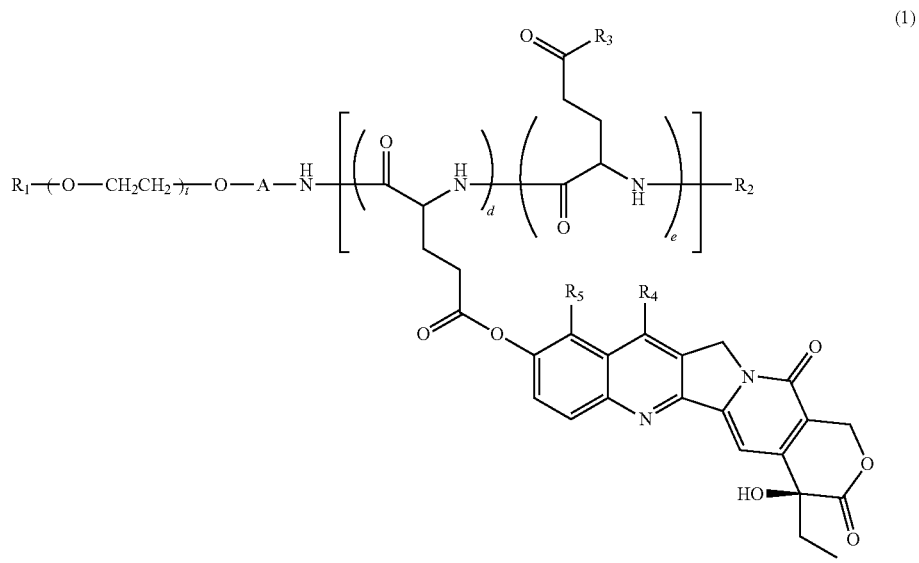

(1)

wherein $R_1$ represents a hydrogen atom or a (C1-C6) alkyl group which may have a substituent; A represents a (C1-C6) alkylene group; $R_2$ represents any one selected from the group consisting of a hydrogen atom, a (C1-C6) acyl group which may have a substituent, and a (C1-C6) alkoxycarbonyl group which may have a substituent; $R_3$ represents a hydroxyl group and/or $N(R_6)CONH(R_7)$; $R_6$ and $R_7$ may be identical or different, and each represents a (C1-C8) alkyl group which may be substituted with a tertiary amino group; $R_4$ represents any one selected from the group consisting of a hydrogen atom, a (C1-C6) alkyl group which may have a substituent, and a silyl group which may have a substituent; $R_5$ represents a hydrogen atom or a (C1-C6) alkyl group which may have a substituent; t represents an integer from 45 to 450; d and e each represent an integer, such that (d+e) represents an integer from 6 to 60, and the proportion of d with respect to (d+e) is 1% to 100%, the proportion of e is 0% to 99%; and the polyglutamic acid segment have a polyglutamic acid segment structure in which glutamic acid units having the camptothecin derivative bonded thereto, and glutamic acid units having $R_3$ groups bonded thereto are each independently arranged in a random fashion.

arylsulfonyl group, a sulfamoyl group, an alkoxy group, an aryloxy group, an acyloxy group, an alkoxycarbonyloxy group, a carbamoyloxy group, a substituted or unsubstituted amino group, an acylamino group, alkoxycarbonylamino group, a ureido group, a sulfonylamino group, a sulfamoylamino group, a formyl group, an acyl group, a carboxyl group, an alkoxycarbonyl group, a carbamoyl group, and a silyl group. The position of substitution on the aromatic ring may be the ortho-position, the meta-position, or the para-position. An amino group, a dialkylamino group, an alkoxy group, a carboxyl group, and a formyl group are preferred.

Preferred examples of $R_1$ may include a methyl group, an ethyl group, a n-propyl group, an isopropyl group, a n-butyl group, a s-butyl group, a t-butyl group, a benzyl group, a 2,2-dimethoxyethyl group, a 2,2-diethoxyethyl group, and a 2-formylethyl group. An unsubstituted linear, branched or cyclic (C1-C4) alkyl group is preferred. A methyl group, an ethyl group, a n-propyl group, an isopropyl group, a n-butyl group, a s-butyl group, a t-butyl group, and the like are particularly preferred.

In regard to general formula (1), it is preferable to use a polyethylene glycol segment in which the polyethylene glycol moiety in the segment has a molecular weight of 2 kilodaltons to 20 kilodaltons, and more preferably 4 kilodaltons to 15 kilodaltons. That is, t in general formula (1), which is the number of unit repeated structures of an ethyleneoxy group; ($-OCH_2CH_2$) group, represents an integer from 45 to 450. Preferably, t represents an integer from 90 to 340. Meanwhile, regarding the molecular weight of the polyethylene glycol segment, the peak top molecular weight that is determined by a GPC method using polyethylene glycol standards is used.

A in general formula (1), which is a linking group that joins the polyethylene glycol segment and the polyglutamic acid segment, is a (C1-C6) alkylene group. Examples thereof may include a methylene group, an ethylene group, a trimethylene group, a tetramethylene group, and a hexamethylene group. Among them, an ethylene group or a trimethylene group is preferred, and a trimethylene group is particularly preferred.

The polyglutamic acid segment of the polymer compound of the present invention represented by general formula (1) has a structure in which glutamic acid units are polymerized in an α-amide bonded form. However, in that amino acid polymerized structure, glutamic acid units that are polymerized in a γ-amide bonded form may also be included in some part. In regard to the polyglutamic acid segment, the various glutamic acid units may be of L-type or D-type, or they may exist in mixture.

The total number of the glutamic acid units in general formula (1) is represented by expression: (d+e), and is an integer from 6 to 60. Preferably, (d+e) is 8 to 40. Therefore, although the average molecular weight of the polyglutamic acid segment is dependent on the structures of the camptothecin derivative and the $R_3$ group that are bonded to each other as will be described below and the amount of linking groups, the average molecular weight is 0.6 kilodaltons to 15 kilodaltons, and preferably 0.8 kilodaltons to 10 kilodaltons.

The total number of glutamic acid units in the polyglutamic acid segment may be determined by a method for calculating the number of glutamic acid units by H-NMR, an amino acid analysis method, a method for acid-base titration of side chain carboxyl groups, or the like. It is preferable to employ the number of glutamic acid units that determines the amount of the side chain carboxyl groups by an acid-base titration method, using a polyglutamic acid segment before the camptothecin derivative and the $R_3$ group are bonded to a side chain.

The (C1-C6) acyl group which may have a substituent with regard to $R_2$ may be a linear, branched or cyclic (C1-C6) acyl group which may have a substituent. Examples thereof may include a formyl group, an acetyl group, a propionyl group, a butyryl group, and a valeryl group.

Regarding the substituent, the acyl group may include a hydroxyl group, a halogen atom, an amino group, an alkylamino group, a dialkylamino group, an alkoxy group, or an aryl group.

Preferred examples may include a formyl group, an acetyl group, a trichloroacetyl group, a trifluoroacetyl group, a propionyl group, a pivaloyl group, a benzylcarbonyl group, and a phenethylcarbonyl group. A linear, branched or cyclic (C1-C4) acyl group which may have a substituent is preferred, and an acetyl group, a trichloroacetyl group and a trifluoroacetyl group are preferred.

The (C1-C6) alkoxycarbonyl group which may have a substituent with regard to $R_2$ may be a linear, branched or cyclic (C1-C6) alkoxycarbonyl group which may have a substituent. Regarding the substituent, the alkoxycarbonyl group may include a hydroxyl group, a halogen atom, an amino group, an alkylamino group, a dialkylamino group, an alkoxy group, or an aryl group.

Preferred examples may include a methoxycarbonyl group, an ethoxycarbonyl group, a t-butoxycarbonyl group, a benzyloxycarbonyl group, and a 9-fluorenylmethyloxycarbonyl group.

Regarding $R_2$, it is preferable to use a hydrogen atom or a linear, branched or cyclic (C1-C4) acyl group which may have a substituent. $R_2$ is particularly preferably a hydrogen atom, an acetyl group, a trichloroacetyl group, or a trifluoroacetyl group.

In regard to general formula (1), $R_3$ represents a hydroxyl group and/or $-N(R_6)CONH(R_7)$. That is, a glutamic acid unit in which a side chain carboxyl group is $R_3$ is a glutamic acid unit in which a side chain is unmodified, and/or a glutamic acid unit in which a urea derivative is bonded to a side chain.

$R_6$ and $R_7$ may be identical or different, and each represents a linear, branched or cyclic (C1-C8) alkyl group which may be substituted with a tertiary amino group. Examples of the (C1-C8) alkyl group for $R_6$ and $R_7$ may include a methyl group, an ethyl group, a n-propyl group, an isopropyl group, a n-butyl group, a t-butyl group, a cyclopropyl group, a cyclohexyl group, and a n-octyl group.

Examples of the linear, branched or cyclic (C1-C8) alkyl group which may be substituted with a tertiary amino group may include a 2-dimethylaminoethyl group and a 3-dimethylaminopropyl group.

Preferred examples of $R_6$ and $R_7$ may include an ethyl group, an isopropyl group, a cyclohexyl group, and a 3-dimethylaminopropyl group. More preferred examples may include a case in which $R_6$ and $R_7$ are both isopropyl groups, a case in which $R_6$ and $R_7$ are both cyclohexyl groups, and a case in which $R_6$ and $R_7$ are an ethyl group and a 3-dimethylaminopropyl group, respectively.

As will be described below, $-N(R_4)CONH(R_7)$ with regard to $R_3$ is a glutamic acid side chain-modifying group that is produced as a side product by using a carbodiimide-based condensing agent when the block copolymer related to general formula (1) having a camptothecin derivative bonded thereto is synthesized. Therefore, these $R_6$ and $R_7$ become identical with the alkyl substituent of the carbodiimide-based condensing agent used therein. That is, when diisopropylcarbodiimide (DIPCI) is used as a carbodiimide condensing agent, $R_6$ and $R_7$ both become isopropyl groups. When 1-ethyl-3-(3-dimethylaminopropyl)carbodiimide hydrochloride (WSC) is used, $R_6$ and $R_7$ become mixed substituents of an ethyl groups and a 3-dimethylaminopropyl group. In this case, there exist a case in which $R_3$ is an ethyl group and $R_7$ is a 3-dimethylaminopropyl group, and the case of vice versa, and a $-N(R_6)CONH(R_7)$ group in which these groups are co-present in one molecule is also acceptable.

In regard to general formula (1), $R_3$ may be a hydroxyl group. That is, the polyglutamic acid segment according to the present invention may have a free-form glutamic acid unit that is not bonded to any of the camptothecin derivative and the $-N(R_6)CONH(R_7)$ group. The side chain carboxylic acid in the glutamic acid unit in which $R_3$ is a hydroxyl group is shown to be in a free acid form; however, the side chain carboxylic acid may be in the form of a salt that may be used as a pharmaceutical product, and the side chain carboxylic acid in the form of an alkali metal salt or an alkaline earth metal salt is also included in the present invention. Examples of the alkali metal salt or alkaline earth metal salt may include lithium salt, sodium salt, potassium salt, magnesium salt, and calcium salt. When the pharmaceutical preparation of the present invention is provided as an anticancer agent by parenteral administration, the block copolymer is made into a solution in a pharmaceutically acceptable solubilizing liquid. In that case, the embodiment of the free-form glutamic acid unit is dependent on the pH of the solution and the presence of salts of a buffer solution or the like, and an embodiment of any arbitrary glutamic acid salt may be adopted.

The block copolymer represented by general formula (1) includes a camptothecin derivative bonded to a side chain carboxyl group of a polyglutamic acid segment via an ester bond. The camptothecin derivative is a camptothecin derivative which has, at the 10-position, a hydroxyl group that is provided to the ester bond, and has a $R_4$ group at the 7-position and a $R_5$ group at the 9-position. Any one of $R_4$ and $R_5$ may be a hydrogen atom; however, it is preferable that any one of $R_4$ and $R_5$ represents a substituent other than a hydrogen atom.

$R_4$ represents a hydrogen atom, a (C1-C6) alkyl group which may have a substituent, or a silyl group which may have a substituent.

The (C1-C6) alkyl group which may have a substituent with regard to $R_4$ may be a linear, branched or cyclic (C1-C6) alkyl group which may have a substituent. Regarding the substituent, the alkyl group may include a hydroxyl group, a halogen atom, an amino group, an alkylamino group, a dialkylamino group, an alkoxy group, an aryl group, or the like. Examples thereof may include a methyl group, an ethyl group, a n-propyl group, an isopropyl group, a n-butyl group, a s-butyl group, a t-butyl group, and a benzyl group. A linear, branched or cyclic (C1-C4) alkyl group which may have a substituent is preferred, and an ethyl group is particularly preferred.

Examples of the silyl group which may have a substituent with regard to $R_4$ may include a trimethylsilyl group, a triethylsilyl group, a t-butyldimethylsilyl group, a triisopropylsilyl group, and a t-butyldiphenylsilyl group. A t-butyldimethylsilyl group is preferred.

$R_4$ is preferably a hydrogen atom or an unsubstituted (C1-C6) alkyl group. A hydrogen atom or an ethyl group is particularly preferred.

$R_5$ represents a hydrogen atom or a (C1-C6) alkyl group which may have a substituent.

The (C1-C6) alkyl group which may have a substituent with regard to $R_5$ may be a linear, branched or cyclic (C1-C6) alkyl group which may have a substituent. Regarding the substituent, the alkyl group may include a hydroxyl group, a halogen atom, an amino group, an alkylamino group, a dialkylamino group, an alkoxy group, an aryl group, or the like. Examples thereof may include a methyl group, an ethyl group, a n-propyl group, an isopropyl group, a n-butyl group, a s-butyl group, a t-butyl group, a benzyl group, and a dimethylaminomethyl group.

$R_5$ is preferably a hydrogen atom or a (C1-C6) alkyl group having an amino group. A hydrogen atom or a dimethylaminomethyl group is particularly preferred.

The camptothecin derivative bonded to general formula (1) is preferably a linking residue of 7-ethyl-10-hydroxycamptothecin and/or nogitecan (9-dimethylaminomethyl-10-hydroxycamptothecin). That is, the camptothecin derivative is preferably a linking residue to which 7-ethyl-10-hydroxycamptothecin in which $R_4$ is an ethyl group and $R_5$ is a hydrogen atom, is bonded via an ester bond. Alternatively, the camptothecin derivative is preferably a linking residue to which nogitecan (9-dimethylaminomethyl-10-hydroxycamptothecin) in which $R_4$ is a hydrogen atom and $R_5$ is a dimethylaminomethyl group, is bonded via an ester bond. The camptothecin derivative is particularly preferably a linking residue to which 7-ethyl-10-hydroxycamptothecin in which $R_4$ is an ethyl group and $R_5$ is a hydrogen atom, is bonded via an ester bond.

The block copolymer described in general formula (1) of the present invention preferably includes multiple camptothecin derivatives. The camptothecin derivatives that are bonded to the same molecular chain of the block copolymer may be identical compounds, or multiple kinds of compounds may exist in mixture. However, it is preferable that the camptothecin derivatives bonded to the same molecular chain of the block copolymer are identical compounds.

In regard to general formula (1), the polyglutamic acid segment is such that for various glutamic acid units, a glutamic acid unit to which a camptothecin derivative is bonded to a side chain carboxyl group, and a glutamic acid unit to which the $R_3$ group is bonded to a side chain carboxyl group exist each independently in a random arrangement. Since the $R_3$ group may be a hydroxyl group and/or —N($R_4$)CONH($R_7$), the polyglutamic acid segment is a polyglutamic acid segment on which a glutamic acid unit having a camptothecin derivative bonded thereto, a glutamic acid unit having the —N($R_6$)CONH($R_7$) bonded thereto, and a glutamic acid unit having a side chain that is a free carboxyl group or a salt thereof, each independently exist in a random arrangement.

According to the present invention, the glutamic acid unit having a camptothecin derivative bonded thereto is an essential segment constitution. For the glutamic acid unit having a camptothecin derivative bonded thereto in general formula (1), the amount of existence thereof is represented by d, and the glutamic acid unit occupies 1% to 100% of the total degree of polymerization of glutamic acid segments. The existence ratio of d in the polyglutamic acid segment is preferably 20% to 70%. The amount of bonding of the camptothecin derivative determines the content of the active ingredient at the time of use of the block copolymer as a pharmaceutical product, and significantly affects the pharmacokinetics in the body after administration, thereby being involved in the manifestation of efficacy or side effects.

On the other hand, the $R_3$ group-bonded glutamic acid unit is an optional segment constitution. That is, the glutamic acid unit to which a camptothecin derivative is not bonded is the relevant $R_3$ group-bonded glutamic acid unit. Regarding the $R_3$ group-bonded glutamic acid unit in regard to general formula (1), the amount of existence thereof is represented by e, and the glutamic acid occupies 0% to 99% of the total degree of polymerization of the glutamic acid segments. The existence ratio of e in the polyglutamic acid segment is preferably 30% to 80%. Furthermore, in regard to the block copolymer related to General Formula (1), the percentage content of the camptothecin derivative is preferably 10% to 60% by mass.

The content of the camptothecin derivative may be measured by quantitatively analyzing the camptothecin derivative that has been released by cleaving the ester bond bonded to the glutamic acid unit through hydrolysis. More preferably, the percentage content of the camptothecin derivative is 10% to 50% by mass, and particularly preferably 15% to 40% by mass.

The $R_3$ group is a hydroxyl group and/or —N($R_4$)CONH($R_7$). This —N($R_6$)CONH($R_7$) is an optional substituent, and the glutamic acid unit to which a camptothecin derivative is not bonded is preferably such that a hydroxyl group is a main substituent. With respect to the total degree of polymerization of glutamic acids in the polyglutamic acid segment, (d+e), the existence ratio of the glutamic acid unit in which $R_3$ is a hydroxyl group is preferably 15% to 60%, and the extent ratio of the glutamic acid unit in which $R_3$ is —N($R_6$)CONH($R_7$) is preferably 0% to 50%.

When the $R_3$ group is a —N($R_6$)CONH($R_7$) group, the percentage content of the —N($R_6$)CONH($R_7$) group is preferably 1% to 15% by mass, and the content of the —N($R_6$)CONH($R_7$) group may be determined by a method of measuring the content by quantitatively analyzing free urea residues by cleaving the amide bond bonded to the glutamic acid unit through hydrolysis, or by measuring the percentage content of the N($R_6$)CONH($R_7$) group by $^1$H-NMR. More preferably, the percentage content of the —N($R_6$)CONH($R_7$) group is 2% to 10% by mass.

Meanwhile, the block copolymer related to general formula (1) of the present invention has a physical property of forming associative aggregates in an aqueous solution. In order to obtain a stable associative aggregate-forming ability, the ability may be appropriately set based on the balance between the hydrophilicity of the polyethylene glycol segment and the hydrophobicity of the polyglutamic acid segment. Preferably, a block copolymer in which t of the polyethylene glycol segment in general formula (1) is an integer from 90 to 340 and the total number of glutamic acid unit, (d+e), is an integer from 8 to 40, is used, and a block copolymer in which the existence ratio of d, which is the amount of existence of the glutamic acid unit having a camptothecin derivative bonded thereto, in the polyglutamic acid segment is 20% to 70%, is used.

Next, the method for producing a block copolymer represented by general formula (1) according to the present invention will be explained by taking an example.

The relevant block copolymer may be produced by bonding a camptothecin derivative having a hydroxyl group at the 10-position to "a block copolymer in which a polyethylene glycol segment and a free-form polyglutamic acid segment are linked", through an esterification reaction. Optionally, when a —N($R_6$)CONH($R_7$) group related to $R_3$ is subjected to a bonding reaction, the block copolymer having a camptothecin derivative bonded thereto according to the present invention may be produced. The method for a bonding reaction between this camptothecin derivative having a hydroxyl group at the 10-position and the optional —N($R_6$)CONH($R_7$) group is not particularly limited. A camptothecin derivative having a hydroxyl group at the 10-position may be first subjected to a bonding reaction, and then the —N($R_6$)CONH($R_7$) group may be subjected to a bonding reaction; the processes may also be carried out in a reverse order; or the bonding reactions may also be carried out simultaneously.

Examples of the method for constructing the "block copolymer in which a polyethylene glycol segment and a free-form polyglutamic acid segment are linked" may include a method of bonding a polyethylene glycol segment to a polyglutamic acid segment, and a method of sequentially polymerizing polyglutamic acid to a polyethylene glycol segment, and any of the methods may be employed.

The method for synthesizing a block copolymer represented by general formula (1) according to the present invention will be explained by taking an example in which the camptothecin derivative is 7-ethyl-10-hydroxycamptothecin, and the hydroxyl group at the 10-position of the camptothecin derivative and a carboxyl group of the glutamic acid segment of the block copolymer are bonded by an ester bond. Meanwhile, the relevant camptothecin derivative-bonded block copolymer may be produced by the method disclosed in WO 2004/039869. An outline of the production method described in this document will be given below.

Regarding the method for synthesizing the "block copolymer in which a polyethylene glycol segment and a free-form polyglutamic acid segment are linked", a method of constructing a polyglutamic acid structural moiety at the terminal of the polyethylene glycol segment side, by sequentially reacting N-carbonyl glutamic acid anhydride with a polyethylene glycol compound having one terminal modified with an alkoxy group and the other terminal modified with an amino group, may be employed. In this case, regarding the N-carbonyl glutamic acid anhydride, it is preferable that the carboxyl group in a side chain of glutamic acid is a glutamic acid derivative modified with an appropriate carboxylic acid protective group. The carboxylic acid protective group is not particularly limited; however, an ester protective group is preferred.

More specifically, a method of producing a block copolymer having a polyethylene glycol segment and a polyglutamic acid segment through sequential polymerization, by sequentially reacting γ-benzyl-N-carbonyl glutamic acid anhydride with a polyethylene glycol having one terminal modified with a methoxy group and the other terminal modified with an amino group, may be employed. At this time, the degree of polymerization of glutamic acid in the polyglutamic acid segment may be controlled by adjusting the use equivalent of the γ-benzyl-N-carbonyl glutamic anhydride.

Subsequently, benzyl groups of the polyglutamic acid segment are deprotected by an appropriate method, and thereby the "block copolymer in which a polyethylene glycol segment and a polyglutamic acid segment are linked" may be produced. Regarding a deprotection reaction for benzyl groups, a hydrolysis reaction under alkali conditions and a hydrogenation reduction reaction may be employed.

Next, 7-ethyl-10-hydroxycamptothecin is subjected to a condensation reaction with the "block copolymer in which a polyethylene glycol segment and a free-form polyglutamic acid segment are linked", in the co-presence of a carbodiimide condensing agent. When this method is used, 7-ethyl-10-hydroxycamptothecin and the —N($R_6$)CONH($R_7$) group may be simultaneously bonded to the block copolymer, and therefore, this method is an advantageous reaction. Meanwhile, in regard to the relevant condensation reaction, the amount of bonding of the camptothecin derivative may be controlled by adjusting the use equivalent amount of 7-ethyl-10-hydroxycamptothecin. Furthermore, the amount of introduction of the —N($R_6$)CONH($R_7$) group may be controlled by adjusting the use equivalent amount of the carbodiimide condensing agent.

Residual glutamic acid units in which side chain carboxyl groups are not chemically modified, excluding the glutamic acid units having the camptothecin derivative and the —N($R_6$)CONH($R_7$) group bonded thereto, constitute the glutamic acid units in which $R_3$ is a hydroxyl group. The amount of the glutamic acid units in which $R_3$ is a hydroxyl group may be controlled by means of the use equivalent amounts of the camptothecin derivative and the carbodiimide condensing agent.

Meanwhile, regarding the carbodiimide condensing agent used herein, any condensing agent capable of ester bonding the camptothecin derivative to a side chain carboxyl group of a glutamic acid unit, may be used without any particular limitations. Preferred examples may include dicyclohexylcarbodiimide (DCC), diisopropylcarbodiimide (DIPCI), and l-ethyl-3-(3-dimethylaminopropyl)carbodiimide hydrochloride (WSC). At the time of the condensation reaction, a reaction auxiliary agent such as N,N-dimethylaminopyridine (DMAP) may also be used. Meanwhile, when DCC is used as a carbodiimide condensing agent, $R_6$ and $R_7$ are cyclohexyl groups; when DIPCI is used, $R_6$ and $R_7$ are isopropyl groups; and when WSC is used, $R_6$ and $R_7$ are a mixture of an ethyl group and a 3-dimethylaminopropyl group.

When an appropriate amount of 7-ethyl-10-hydroxycamptothecin and an appropriate amount of a —N($R_6$)CONH ($R_7$) group as an optional substituent for $R_3$ are bonded, through the reaction described above, to a glutamic acid side chain of the "block copolymer in which a polyethylene glycol segment and a free-form polyglutamic acid segment are linked", and then a purification process is carried out as appropriate, the block copolymer having a camptothecin derivative bonded thereto according to the present invention may be synthesized. Regarding the purification process, it is preferable to produce a side chain hydroxyl group-containing form of polyglutamic acid into a free acid form, while simultaneously removing residual amine components by means of a cation exchange resin or the like.

The block copolymer having a camptothecin derivative bonded thereto as represented by general formula (1) has a performance of slowly releasing the camptothecin derivative in a phosphate buffer saline (PBS) solution and continuously releasing the camptothecin derivative. For example, when the camptothecin derivative is 7-ethyl-10-hydroxycamptothecin and is an ester-bonded form by means of the hydroxyl group at the 10-position, the block copolymer has a physical property of slowly releasing 7-ethyl-10-hydroxycamptothecin when this is administered into the body. Low molecular weight drug that are generally used for clinical purposes exhibit the maximum blood concentrations of the drugs immediately after being administered, and then are relatively rapidly discharged out of the body. In contrast, the relevant camptothecin derivative-bonded block copolymer is a preparation characterized in that in order to slowly dissociate 7-ethyl-10-hydroxycamptothecin as an active ingredient, the block copolymer exhibits a persistent blood concentration profile without excessively increasing the blood concentration of the active ingredient in the blood after administration.

Furthermore, in the relevant camptothecin derivative-bonded block copolymer, the polyethylene glycol segment is hydrophilic. On the other hand, since the polyglutamic acid segment includes the hydrophilic camptothecin derivative, the relevant camptothecin derivative-bonded block copolymer has associative properties based on a hydrophobic interaction between the polyglutamic acid segments in an aqueous solution. Therefore, an aqueous solution of the block copolymer forms core-shell type micellar associates, in which hydrophobic polyglutamic acid segments form a core by associative aggregates, while hydrophilic polyethylene glycol segments cover the circumference of the core to form an outer shell to thereby form a shell layer.

In regard to the micellar associates, the formation of associates may be checked by measuring the scattered light intensity using laser light or the like, and thus, the associate-forming properties may be evaluated based on the scattered light intensity value. For example, the scattered light intensity may be directly used as a physical property value for the associative aggregate-forming properties. In regard to an aqueous solution of the block copolymer, for example, an aqueous solution of the block copolymer at a concentration of 0.01 to 100 mg/mL exhibits a scattered light intensity value of several thousand cps to several hundred thousand cps, and it is acknowledged that associative aggregates are formed. Furthermore, the molecular weight of the associative aggregates based on high molecular weight standards of polyethylene glycol or the like may be estimated from the scattered light intensity. It may be calculated that the aqueous solution of the block copolymer includes associative aggregates having a total molecular weight of 1,000,000 or more. Therefore, it is speculated that the nanoparticles are formed as a result of the association of a plurality of the block copolymer molecules, such as several dozen molecules to several hundred molecules. Furthermore, an aqueous solution of the block copolymer has a physical property of forming nanoparticulate bodies of several nanometers to several hundred nanometers according to a particle size analysis based on a dynamic light scattering analysis.

The block copolymer that forms nanoparticles as associative aggregates in an aqueous solution is such that when administered into the body, the block copolymer is distributed in the body in the form of the above-mentioned associative nanoparticles in blood. A high molecular weight compound or a nanoparticulate object has a significantly different pharmacokinetic behavior or tissue distribution in the body, compared to low molecular weight drugs that are conventionally used. Therefore, it is known in regard to the camptothecin derivative-bonded block copolymer capable of forming associative nanoparticles, that the retention in the body or the distribution in the tissue is determined depending on the associate molecular weight or the particle size of the nanoparticles, and the block copolymer is retained and distributed particularly in tumor tissues. From this point of view, the camptothecin derivative-bonded block copolymer is an antitumor preparation which has pharmaceutical efficacy exhibiting characteristics and side effect exhibiting characteristics that are completely different from those of conventional low molecular weight camptothecin preparations, and is thus capable of providing a new therapeutic method in clinical use of camptothecin derivatives. Therefore, since the relevant block copolymer is in the form of nanoparticles which are formed by particular associative properties and are controlled to have a desired associate molecular weight and a desired particle size, it is important to obtain pharmacokinetics and a distribution in the tissue that are preferable as an antitumor agent, and the formation of nanoparticles having a desired associate molecular weight and a desirable particle size may be listed as an important product quality management item for performance demonstration.

According to the present invention, a saccharide is used as an additive in the pharmaceutical preparation including the block copolymer as an active ingredient. Regarding this saccharide, those monosaccharides, disaccharides, and sugar alcohols that are used as pharmaceutical additives may be used.

Examples of the monosaccharides and disaccharides may include maltose, glucose, lactose, fructose, trehalose, sucrose, arabinose, isomaltose, galactosamine, galactose, xylose, glucosamine, gentiobiose, kojibiose, cellobiose, sophorose, thioglucose, turanose, deoxyribose, nigerose, palatinose, fucose, mannose, melibiose, rhamnose, and laminaribiose.

Examples of the sugar alcohols may include mannitol, sorbitol, inositol, xylitol, magnesium gluconate, maltitol, and meglumine.

Regarding the saccharide additive used therein, any saccharide additive having the purity that is used in pharmaceutical preparations may be used without any particular limitations. These may be used singly, or may be used as mixtures of these compounds.

Regarding the saccharide according to the present invention, it is preferable to use one or more kinds of monosaccharides, disaccharides, and sugar alcohols selected from the group consisting of maltose, glucose, lactose, fructose, trehalose, sucrose, mannitol, sorbitol, inositol, xylitol, and magnesium gluconate. These saccharides are saccharide additives that may maintain, in a pharmaceutical preparation including the above-mentioned block copolymer as an active ingredient, the associating properties of the block copolymer for a long time period. Particularly preferred are monosaccharides and disaccharides, and it is preferable to use one or more kinds selected from the group consisting of maltose, glucose, lactose, fructose, trehalose, and sucrose.

In regard to the present pharmaceutical preparation, it is preferable to use the saccharide in an amount of 10 to 500 parts by mass with respect to 1 part by mass of the camptothecin derivative content of the block copolymer. If the dose of the saccharide is smaller than 10 parts by mass with respect to the camptothecin derivative, there is a risk that the effect of stabilizing the retention of the association properties of the block copolymer may not be sufficiently obtained. Meanwhile, from the viewpoint of the stabilizing effect, there is no particular problem with the upper limit of the amount of use of the saccharide; however, in view of the validity of the dose as a pharmaceutical preparation, it is preferable to set the upper limit to be about 500 parts by mass. More preferably, the amount of use of the saccharide is 20 to 500 parts by mass with respect to 1 part by mass of the camptothecin derivative content of the block copolymer, and it is particularly preferable to use the saccharide in an amount of 20 to 300 parts by mass.

Furthermore, it is preferable to use the saccharide in an amount of 2 to 100 parts by mass with respect to 1 part by mass of the block copolymer. More preferably, the amount of use is 4 to 100 parts by mass with respect to 1 part by mass of the block copolymer, and it is particularly preferable to use the saccharide in an amount of 4 to 60 parts by mass.

The present invention is an invention is a pharmaceutical preparation containing the camptothecin derivative-bonded block copolymer as an active ingredient, and, an invention related to a pharmaceutical unit preparation obtained by filling the block copolymer into a predetermined dosage form at an arbitrary content.

In the case of producing a pharmaceutical preparation, usually, a preparation formulation that is made durable against long-term storage using pharmaceutically acceptable additives, is considered in view of the chemical stability of the active ingredient. In the case of a pharmaceutical preparation including the camptothecin derivative-bonded block copolymer of the present invention as an active ingredient, since the property of forming nanoparticles when made into an aqueous solution is an important product quality management item, it is necessary to perform formulation of a preparation while considering the stability of the nanoparticle-forming properties as well.

The associate-forming properties of a pharmaceutical preparation including the camptothecin derivative-bonded block copolymer of the present invention as an active ingredient, for example, may be evaluated using a measuring instrument capable of measuring the laser scattered light intensity, by taking the scattered light intensity as an index.

Specifically, an aqueous solution of the pharmaceutical preparation including a camptothecin derivative-bonded block copolymer may be used as a measurement sample, and the measured value of the scattered light intensity of the sample may be used as the physical property value of the associate-forming properties.

Regarding the measuring instrument for a scattered light intensity analysis, for example, measurement may be made using a dynamic light scattering photometer manufactured by Otsuka Electronics Co., Ltd., DLS-8000DL.

Regarding the method for evaluating the storage stability of the pharmaceutical preparation including a camptothecin derivative-bonded block copolymer as an active ingredient, the pharmaceutical preparation is stored for 4 weeks at 40° C. under light-shielded conditions, an analysis of the scattered light intensity of the pharmaceutical preparation is performed, and the extent of change in the scattered light intensity value is considered as the ratio of change in the associate-forming properties. Thus, the ratio of change in the associate-forming properties is evaluated.

The present pharmaceutical preparation including the camptothecin derivative-bonded block copolymer as an active ingredient is such that when the pharmaceutical preparation has been stored for 4 weeks at 40° C. under light-shielded conditions, the ratio of change in the associate formation based on the associate molecular weight as an index is 20% or lower. A pharmaceutical product characterized by the associate-forming properties has a problem that the associate-forming properties are markedly deteriorated during the storage of the preparation, and when desired associative nanoparticles may not be formed, the effectiveness of the camptothecin derivative-bonded block copolymer is lowered. Therefore, it is required that the pharmaceutical preparation is a preparation in which the associate-forming properties are not deteriorated in the state of being stored as a pharmaceutical product preparation.

The ratio of change in the associate formation according to the present invention is the absolute value of the increase or decrease ratio of the measured value of scattered light intensity after storage of the pharmaceutical preparation including the block copolymer for 4 weeks at 40° C., with respect to the initial value of the scattered light intensity value of the pharmaceutical preparation. According to the present invention, the ratio of change in the associate formation is determined according to the type and dose of the saccharide used. Therefore, the pharmaceutical preparation according to the present invention may be produced by appropriately adjusting the type and dose of the saccharide based on the analyzed value of the scattered light intensity as an index. The present pharmaceutical preparation is more preferably such that the ratio of change in the associate formation is 10% or lower.

The present pharmaceutical preparation has an effect of exhibiting chemical stability, with suppressed liberation of the bonded camptothecin derivative from the block copolymer. That is, in regard to the pharmaceutical preparation, any free camptothecin derivative produced as a result of dissociation of the bonded camptothecin derivative corresponds to impurities and it is desirable that the free camptothecin derivative is reduced as much as possible. The present pharmaceutical preparation has excellent chemical stability of suppressing dissociation of the bonded camptothecin derivative, suppresses a decrease in the content of the active ingredient, and exhibits a performance of having excellent preparation storage stability.

In regard to the present pharmaceutical preparation, when the ratio of change in the camptothecin derivative liberation based on the amount of liberation of the camptothecin derivative from the block copolymer as an index is evaluated, when the pharmaceutical preparation has been stored for 4 weeks at 40° C. under light-shielded conditions, the ratio of change in the camptothecin derivative bonding of the block copolymer is 8.0 times or less. The camptothecin derivative liberation ratio is represented by the ratio of the percentage of camptothecin derivative liberation after storage for 4 weeks at 40° C. with respect to the initial percentage of camptothecin derivative liberation. Meanwhile, the amount of liberation of the camptothecin derivative may be quantitatively analyzed by high performance liquid chromatography (HPLC) method by using the pharmaceutical preparation as a sample. According to the present invention, the ratio of change in the camptothecin derivative liberation is determined according to the type and dose of the saccharide used. Therefore, the pharmaceutical preparation according to the present invention may be produced by appropriately adjusting the type and dose of the saccharide based on the amount of free camptothecin derivative as an index. The present pharmaceutical preparation is more preferably such that the ratio of change in the camptothecin derivative liberation is 5.0 times or less.

In order to produce a pharmaceutical preparation including the present camptothecin derivative-bonded block copolymer as an active ingredient, the pharmaceutical preparation having a low ratio of change in associates and excellent preparation storage stability, it is desirable that when the pharmaceutical preparation is made into an aqueous solution containing the camptothecin derivative at a concentration of 1 mg/mL, the pH of the aqueous solution is 3.0 to 6.0.

In order to adjust the pH of the present pharmaceutical preparation to 3.0 to 6.0, a pH adjusting agent may be used. Regarding the pH adjusting agent used for the present invention, any acid that may be used as a pharmaceutical additive may be used without any particular limitations, and examples thereof may include hydrochloric acid, sulfuric acid, phosphoric acid, citric acid, tartaric acid, malic acid, mesylic acid, tosylic acid, and besylic acid. A buffering agent including such an acidic additive as a main component and including an alkali metal salt, an alkaline earth metal salt, or an ammonium salt in addition to the acidic additive, may also be used.

Preferably, hydrochloric acid, phosphoric acid, citric acid, and tartaric acid may be used, and it is preferable to use them in an appropriate amount of addition so as to obtain a pH of 3.0 to 5.0 as an aqueous solution of the pharmaceutical preparation.

The pharmaceutical preparation of the present invention is preferably a preparation that is administered into the blood vessels for injection or infusion, and is preferably an injectable preparation that may be intravenously administered. The dosage form is preferably a dosage form such as a freeze-dried preparation, an injectable liquid preparation that may be made into an injectable solution by diluting at the time of use, or a diluted solution preparation that may be directly administered.

That is, in the case of being administered as a pharmaceutical product, the pharmaceutical preparation is usually used as a solution of the relevant pharmaceutical preparation using water, physiological saline, a 5% aqueous solution of glucose or mannitol, a water-soluble organic solvent (for example, a single solvent such as glycerol, ethanol, dimethyl sulfoxide, N-methylpyrrolidone, polyethylene glycol, or Cremophor, or a mixed solvent of these), or the like.

When the chemical stability and associate-forming stability of the relevant camptothecin derivative-bonded block copolymer are considered, the pharmaceutical preparation is preferably a freeze-dried preparation.

The pharmaceutical preparation of the present invention may include pharmaceutically acceptable additives that are conventionally used. Examples of the additives to be used may include a binder, a lubricating agent, a disintegrant, a solvent, an excipient, a solubilizing agent, a dispersant, a stabilizer, a suspending agent, a preservative, a soothing agent, a colorant, and a fragrance.

In the case of producing a freeze-dried preparation, an aqueous solution is produced using the camptothecin derivative-bonded block copolymer as a pharmaceutically active ingredient, together with optional preparation additives, and a medicinal liquid is produced by adjusting the pH of the aqueous solution. When this is preferably subjected to filtration and sterilization, subsequently dispensed into a preparation vial, and freeze-dried, the pharmaceutical preparation may be made into a freeze-dried preparation. For the adjustment of pH, a pH adjusting agent may be used, or pH adjustment may be carried out with the active ingredient itself, using a camptothecin derivative-bonded block copolymer including, as an active ingredient, a glutamic acid unit in which a side chain is a free-form carboxylic acid.

Meanwhile, in the case of producing the pharmaceutical preparation into an injectable liquid preparation, an aqueous solution is prepared by adding the saccharide additive for preparation to the block copolymer. Subsequently, the aqueous solution is made into a medicinal liquid having its pH adjusted, and an injectable liquid preparation may be produced preferably by subjecting this medicinal liquid to filtration and sterilization and then dispensing the resultant into a preparation container. For the adjustment of pH, a pH adjusting agent may be used, or pH adjustment may be carried out with the active ingredient itself.

This pharmaceutical preparation is a pharmaceutical preparation which has a low ratio of change in the scattered light intensity analyzed as an aqueous solution even if the pharmaceutical preparation is stored for 4 weeks at 40° C. under light-shielded conditions, is stable in connection with the associate formation rate, exhibits a low level of liberation of the camptothecin derivative, and has excellent principal drug stability.

A pharmaceutical preparation including the camptothecin derivative-bonded block copolymer of the present invention as an active ingredient may be utilized as a pharmaceutical product including a camptothecin derivative as an active ingredient. It is particularly preferable to use the pharmaceutical preparation as an antitumor agent for cancer chemotherapy.

The application of the pharmaceutical preparation of the present invention is not particularly limited as long as the lesion is a carcinoma to which the camptothecin derivative provides a therapeutic effect. However, specific examples may include small cell lung cancer, non-small cell lung cancer, cervical cancer, ovarian cancer, gastric cancer, colorectal cancer, breast cancer, squamous cell carcinoma, malignant lymphoma, infant malignant solid tumor, pancreatic cancer, and multiple myeloma.

The dosage of the pharmaceutical preparation of the present invention may definitely vary depending on the gender, age, physiological condition and pathologic condition of the patient, or the like; however, the pharmaceutical preparation is usually parenterally administered in an amount of 0.01 to 500 mg/m$^2$ (body surface area), and preferably 0.1 to 250 mg/m$^2$, in terms of the camptothecin derivative, per day for an adult. It is preferable that administration by injection is performed at the vein, artery, lesion (tumor part), or the like.

EXAMPLES

Synthesis Example 1

Synthesis of 7-ethyl-10-hydroxycamptothecin-bonded block copolymer (Compound 1), in which in general formula (1), $R_1$=methyl group, $R_2$=acetyl group, A=trimethylene group, $R_6$=$R_7$=isopropyl group, (d+e)=24, t=273, proportion of d with respect to (d+e) is 44%, proportion of e is 56% (percentage content of glutamic acid unit with hydroxyl group for $R_3$ is 30%, and percentage content of glutamic acid unit with —N($R_6$)CONH($R_7$) for $R_3$ is 26%).

Compound 1 was synthesized based on the description of WO 2004/39869. That is, a methoxypolyethylene glycol-polyglutamic acid block copolymer (a block copolymer having a molecular weight of 12 kilodaltons, including a methoxypolyethylene glycol structural moiety with a methyl group on one terminal and an aminopropyl group on the other terminal, and a polyglutamic acid structural moiety having the N-terminal modified with an acetyl group and having a degree of polymerization of 24, with the linking group being a trimethylene group, was reacted with 7-ethyl-10-hydroxycamptothecin (EHC) using diisopropylcarbodiimide (DIPCI) and N,N-dimethylaminopyridine (DMAP). Subsequently, the reaction product was treated with an ion exchange resin (DOWEX 50 ($H^+$) manufactured by Dow Chemical Company) and was freeze-dried. Thus, Compound 1 was obtained.

Compound 1 thus obtained was subjected to hydrolysis for 10 minutes at room temperatures using an aqueous solution of sodium hydroxide, and then liberated EHC was quantitatively analyzed by a HPLC method to determine the EHC content. The EHC content was 21.0% by mass.

Example 1

A drug solution containing Compound 1 at a concentration of 1 mg/mL in terms of the EHC content and also containing maltose at a content of 50 mg/mL, was produced using water for injection. The pH of the solution was adjusted to 4 using phosphoric acid, and then the solution was sterilized and filtered. The resultant solution was introduced into glass vials in an amount of 3 mL each and was freeze-dried. Subsequently, the glass vials were tightly sealed with rubber stoppers, and this preparation was designated as Example 1.

Example 2

A drug solution having a glucose content of 50 mg/mL was produced by a method similar to that of Example 1, and the drug solution was freeze-dried. This freeze-dried preparation was tightly sealed with rubber stoppers, and the preparation was designated as Example 2.

Example 3

A drug solution having a lactose content of 50 mg/mL was produced by a method similar to that of Example 1, and the drug solution was freeze-dried. This freeze-dried preparation was tightly sealed with rubber stoppers, and the preparation was designated as Example 3.

Example 4

A drug solution having a fructose content of 50 mg/mL was produced by a method similar to that of Example 1, and the drug solution was freeze-dried. This freeze-dried preparation was tightly sealed with rubber stoppers, and the preparation was designated as Example 4.

Example 5

A drug solution having a trehalose content of 50 mg/mL was produced by a method similar to that of Example 1, and the drug solution was freeze-dried. This freeze-dried preparation was tightly sealed with rubber stoppers, and the preparation was designated as Example 5.

Example 6

A drug solution having a sucrose content of 50 mg/mL was produced by a method similar to that of Example 1, and the drug solution was freeze-dried. This freeze-dried preparation was tightly sealed with rubber stoppers, and the preparation was designated as Example 6.

Example 7

A drug solution having a mannitol content of 50 mg/mL was produced by a method similar to that of Example 1, and the drug solution was freeze-dried. This freeze-dried preparation was tightly sealed with rubber stoppers, and the preparation was designated as Example 7.

Example 8

A drug solution having a sorbitol content of 50 mg/mL was produced by a method similar to that of Example 1, and the drug solution was freeze-dried. This freeze-dried preparation was tightly sealed with rubber stoppers, and the preparation was designated as Example 8.

Example 9

A drug solution having an inositol content of 50 mg/mL was produced by a method similar to that of Example 1, and the drug solution was freeze-dried. This freeze-dried preparation was tightly sealed with rubber stoppers, and the preparation was designated as Example 9.

Example 10

A drug solution having a xylitol content of 50 mg/mL was produced by a method similar to that of Example 1, and the drug solution was freeze-dried. This freeze-dried preparation was tightly sealed with rubber stoppers, and the preparation was designated as Example 10.

Example 11

A drug solution having a magnesium gluconate content of 50 mg/mL was produced by a method similar to that of Example 1, and the drug solution was freeze-dried. This freeze-dried preparation was tightly sealed with rubber stoppers, and the preparation was designated as Example 11.

Example 12

A drug solution containing Compound 1 at a concentration of 1 mg/mL in terms of the EHC content and also containing maltose at a content of 50 mg/mL, was produced using water for injection. The pH of the solution was adjusted to 3 using phosphoric acid, and then the solution was sterilized and filtered. The resultant solution was introduced into glass vials in an amount of 3 mL each and was freeze-dried. Subsequently, the glass vials were tightly sealed with rubber stoppers, and this preparation was designated as Example 12.

Example 13

A drug solution containing Compound 1 at a concentration of 1 mg/mL in terms of the EHC content and also containing maltose at a content of 50 mg/mL, was produced using water for injection. The pH of the solution was adjusted to 5 using phosphoric acid, and then the solution was sterilized and filtered. The resultant solution was introduced into glass vials in an amount of 3 mL each and was freeze-dried. Subsequently, the glass vials were tightly sealed with rubber stoppers, and this preparation was designated as Example 13.

Example 14

A drug solution containing Compound 1 at a concentration of 1 mg/mL in terms of the EHC content and also containing maltose at a content of 25 mg/mL, was produced using water for injection. The pH of the solution was adjusted to 4 using phosphoric acid, and then the solution was sterilized and filtered. The resultant solution was introduced into glass vials in an amount of 3 mL each and was freeze-dried. Subsequently, the glass vials were tightly sealed with rubber stoppers, and this preparation was designated as Example 14.

Example 15

A drug solution containing Compound 1 at a concentration of 1 mg/mL in terms of the EHC content and also containing maltose at a content of 100 mg/mL, was produced using water for injection. The pH of the solution was adjusted to 4 using phosphoric acid, and then the solution was sterilized and filtered. The resultant solution was introduced into glass vials in an amount of 3 mL each and was freeze-dried. Subsequently, the glass vials were tightly sealed with rubber stoppers, and this preparation was designated as Example 15.

Comparative Example 1

A drug solution containing Compound 1 at a concentration of 1 mg/mL in terms of the EHC content was produced using water for injection. The pH of the solution was adjusted to 4 using phosphoric acid, and then the solution was sterilized and filtered. The resultant solution was introduced into glass vials in an amount of 3 mL each and was freeze-dried. Subsequently, the glass vials were tightly sealed with rubber stoppers, and this preparation was designated as Comparative Example 1.

Test Example 1: Changes in Scattered Light Intensity of Associative Aggregates of Examples and Comparative Example Under Conditions of Storage at 40° C./for 4 Weeks 3 mL of water for injection was added to each of the preparations of Examples 1 to 15 and Comparative Example 1 immediately after freeze-drying, and a 1 mg/mL solution in terms of the EHC content was produced. The pH of this solution was measured. Subsequently, 3 mL of water for injection was further added thereto. The amount of scattered light of the associative aggregates in this solution was measured by a static light scattering method (SLS method). This was designated as the initial amount of scattered light. The measuring instrument and the measurement conditions are disclosed below.

Separately, the freeze-dried preparations of Examples 1 to 15 and Comparative Example 1 were stored for 4 weeks at 40° C. under light-shielded conditions. Subsequently, 3 mL of water for injection was added to each of the Examples and Comparative Example, and the solution pH was measured. Subsequently, sample production was carried out in the same manner as in the case of the initial sample, and the amount of scattered light of the associative aggregates in the solution of each freeze-dried preparation was measured.

The measurement results of the solution pH and the amount of scattered light at the initial time, and the solution pH and the amount of scattered light after storage at 40° C./for 4 weeks are summarized in Table 1.

Measuring Instrument and Measurement Conditions

Light scattering photometer: DLS-8000DL (manufactured by Otsuka Electronics Co., Ltd.)

Contra-roller: LS-81 (manufactured by Otsuka Electronics Co., Ltd.)

Pump contra-roller: LS-82 (manufactured by Otsuka Electronics Co., Ltd.)

High sensitivity differential refractometer: DRM-3000 (manufactured by Otsuka Electronics Co., Ltd.)

Circulating thermostatic tank: LAUDA E200

Wavelength: 632.8 nm (He—Ne)

Angle: 90°

Ph1: OPEN

Ph2: SLIT

ND Filter: 10%

Dust-cut setting: 10

TABLE 1

Ratios (%) of change in amounts of scattered light of various redissolved micellar samples

| | pH upon redissolution | | Amount of light (cps) | | Ratio (%) of change in amount of scattered light |
|---|---|---|---|---|---|
| | Initial | 40° C./4 w | Initial | 40° C./4 w | |
| Example 1 | 4.0 | 4.1 | 34168 | 33149 | 3.0 |
| Example 2 | 4.0 | 4.3 | 28579 | 28706 | 0.4 |
| Example 3 | 4.0 | 4.3 | 33862 | 36921 | 9.0 |
| Example 4 | 4.0 | 4.3 | 33133 | 35082 | 5.9 |
| Example 5 | 4.0 | 4.3 | 32176 | 33846 | 5.2 |
| Example 6 | 4.0 | 4.2 | 30456 | 29255 | 3.9 |
| Example 7 | 4.0 | 4.2 | 28709 | 31754 | 10.6 |
| Example 8 | 4.0 | 4.1 | 35420 | 30405 | 14.2 |
| Example 9 | 4.1 | 4.3 | 32543 | 32351 | 0.6 |
| Example 10 | 4.0 | 4.2 | 30197 | 32919 | 9.0 |
| Example 11 | 4.0 | 4.8 | 40133 | 37023 | 7.7 |
| Example 12 | 3.0 | 3.1 | 41887 | 39232 | 6.3 |
| Example 13 | 5.0 | 5.2 | 27288 | 27143 | 0.5 |
| Example 14 | 4.0 | 4.3 | 33271 | 32610 | 2.0 |
| Example 15 | 4.0 | 4.3 | 26174 | 28205 | 7.8 |
| Comparative Example 1 | 4.0 | 4.4 | 10629 | 7999 | 24.7 |

From the results of Test Example 1, the ratios of change in the amounts of scattered light of Examples 1 to 15, to which saccharides, sugar alcohols, and sugar derivatives were added, are 14.2% or less at a time point after storage at 40° C./for 4 weeks, and the ratio of change in the amount of scattered light of Comparative Example 1 without any additive is as high as 24.7% at a time point after storage at 40° C./for 4 weeks. From this, it was acknowledged that a stable preparation in which the associative aggregate-forming properties of the camptothecin derivative-bonded block copolymer as an active ingredient undergo less change, may be produced by adding a saccharide or a sugar alcohol thereto.

Test Example 2: Preparation Stability Test
(Camptothecin Derivative Liberation Ratio)

The freeze-dried preparations of Examples 1 to 15 and Comparative Example were stored for 4 weeks at 40° C. under light-shielded conditions. Subsequently, free EHC in each of the pharmaceutical compositions was quantitatively analyzed by a HPLC method, and the preparation stability was evaluated. The results are summarized in Table 2. Furthermore, the extent of free EHC was represented as the ratio of change in free EHC, which was obtained by dividing the amount of free EHC after storage at 40° C. for 4 weeks by the initial value. The measurement results are summarized in Table 2.

TABLE 2

Results of Test Example 2

|  | pH upon redissolution | | ECH liberation ratio (%) | | Ratio of change in EHC liberation |
| --- | --- | --- | --- | --- | --- |
|  | Initial | 40° C./4 w | Initial | 40° C./4 w | ratio |
| Example 1 | 4.0 | 4.1 | 0.15 | 0.18 | 1.20 |
| Example 2 | 4.0 | 4.3 | 0.14 | 0.52 | 3.71 |
| Example 3 | 4.0 | 4.3 | 0.14 | 0.18 | 1.29 |
| Example 4 | 4.0 | 4.3 | 0.14 | 0.36 | 2.57 |
| Example 5 | 4.0 | 4.3 | 0.17 | 0.17 | 1.00 |
| Example 6 | 4.0 | 4.2 | 0.14 | 0.22 | 1.57 |
| Example 7 | 4.0 | 4.2 | 0.16 | 1.16 | 7.25 |
| Example 8 | 4.0 | 4.1 | 0.15 | 0.77 | 5.13 |
| Example 9 | 4.1 | 4.3 | 0.13 | 0.68 | 5.23 |
| Example 10 | 4.0 | 4.2 | 0.14 | 0.62 | 4.43 |
| Example 11 | 4.0 | 4.8 | 0.15 | 1.06 | 7.07 |
| Example 12 | 3.0 | 3.1 | 0.17 | 0.29 | 1.71 |
| Example 13 | 5.0 | 5.2 | 0.20 | 0.58 | 2.90 |
| Example 14 | 4.0 | 4.3 | 0.15 | 0.22 | 1.47 |
| Example 15 | 4.0 | 4.3 | 0.22 | 0.16 | 0.73 |
| Comparative Example 1 | 4.0 | 4.4 | 0.16 | 1.33 | 8.31 |

From the results of Test Example 2, Compound 1, which is a block copolymer having EHC bonded thereto, is preferable as a stabilized preparation because dissociation of EHC is suppressed by the addition of a sugar alcohol or a sugar derivative, such as mannitol, sorbitol, inositol, xylitol, or magnesium gluconate. Dissociation of EHC is further suppressed by the addition of a saccharide such as maltose, glucose, lactose, fructose, trehalose, or sucrose, and thus, Compound 1 is more preferable as a stabilized preparation. Furthermore, it was found that when the amount of addition of a saccharide, a sugar alcohol or a sugar derivative is 5 to 21 times by mass the amount of addition of Compound 1, a noticeably stabilizing effect is provided.

The invention claimed is:

1. A pharmaceutical preparation comprising a block copolymer of a polyethylene glycol segment and a polyglutamic acid segment linked together, the polyglutamic acid segment comprising a glutamic acid unit having a camptothecin derivative bonded thereto; and a saccharide, wherein the block copolymer is a block copolymer represented by Formula (1):

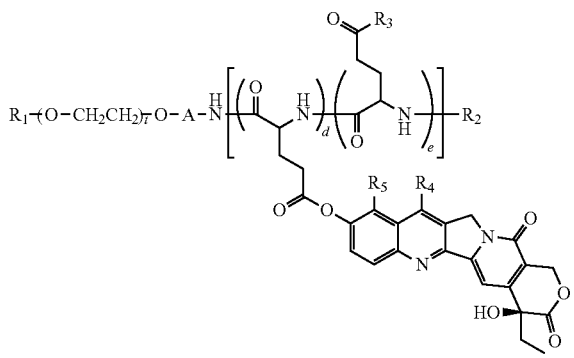

(1)

wherein $R_1$ represents hydrogen atom or a (C1-C6) alkyl group optionally substituted with a substituent; A represents a (C1-C6) alkylene group; $R_2$ represents any one selected from the group consisting of a hydrogen atom, a (C1-C6) acyl group optionally substituted with a substituent, and a (C1-C6) alkoxycarbonyl group optionally substituted with a substituent; $R_3$ represents a hydroxyl group and/or —N($R_6$)CONH($R_7$); $R_6$ and $R_7$ may be identical with or different from each other, each representing a (C1-C8) alkyl group optionally substituted with a tertiary amino group; $R_4$ represents any one selected from the group consisting of a hydrogen atom, a (C1-C6) alkyl group optionally substituted with a substituent, and a silyl group optionally substituted with a substituent; $R_5$ represents a hydrogen atom or a (C1-C6) alkyl group optionally substituted with a substituent; t represents an integer from 45 to 450; d and e each represent an integer, (d+e) represents an integer from 6 to 60, the proportion of d with respect to (d+e) is 1% to 100%, the proportion of e is 0% to 99%; and the polyglutamic acid segment has a polyglutamic acid segment structure having a glutamic acid unit with a camptothecin derivative bonded thereto and a glutamic acid unit with a $R_3$ group bonded thereto, with the glutamic acid units being each independently arranged randomly, wherein the pharmaceutical preparation has a physical property of forming associates based on a plurality of the block copolymer molecules in an aqueous solution, and wherein the ratio of change in the scattered light intensity of the associates of the pharmaceutical preparation obtained after the pharmaceutical preparation has been stored for 4 weeks at 40° C. under light-shielded conditions, is 20% or less.

2. The pharmaceutical preparation according to claim 1, wherein when the pharmaceutical preparation is made into an aqueous solution containing the camptothecin derivative at a concentration of 1 mg/mL, the pH of the aqueous solution is 3.0 to 6.0.

3. The pharmaceutical preparation according to claim 1, further comprising a pH adjusting agent.

4. The pharmaceutical preparation according to claim 1, wherein the saccharide is one or more kinds of saccharides and sugar alcohols selected from the group consisting of maltose, glucose, lactose, fructose, trehalose, sucrose, mannitol, sorbitol, inositol, xylitol, and magnesium gluconate.

5. The pharmaceutical preparation according to claim 4, wherein the saccharide is one or more kinds of saccharides and sugar alcohols selected from the group consisting of maltose, glucose, lactose, fructose, trehalose, and sucrose.

6. The pharmaceutical preparation according to claim 1, wherein the pharmaceutical preparation includes 10 to 500 parts by mass of the saccharide with respect to 1 part by mass of the camptothecin derivative content of the block copolymer.

7. The pharmaceutical preparation according to claim 1, wherein the pharmaceutical preparation is a freeze-dried preparation.

8. The pharmaceutical preparation according to claim 2, further comprising a pH adjusting agent.

* * * * *